(12) United States Patent
Sun et al.

(10) Patent No.: US 10,961,575 B2
(45) Date of Patent: *Mar. 30, 2021

(54) NANOWIRE-BASED SYSTEM FOR ANALYSIS OF NUCLEIC ACIDS

(71) Applicant: APPLIED BIOSYSTEMS, LLC, Carlsbad, CA (US)

(72) Inventors: Hongye Sun, Belmont, CA (US); Steven Fung, Palo Alto, CA (US); Sam Lee Woo, Redwood City, CA (US)

(73) Assignee: APPLIED BIOSYSTEMS, LLC, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/570,093

(22) Filed: Sep. 13, 2019

(65) Prior Publication Data

US 2020/0140942 A1   May 7, 2020

Related U.S. Application Data

(60) Continuation of application No. 15/449,889, filed on Mar. 3, 2017, now Pat. No. 10,415,090, which is a
(Continued)

(51) Int. Cl.
*G01N 27/30* (2006.01)
*C12Q 1/6874* (2018.01)
(Continued)

(52) U.S. Cl.
CPC .......... *C12Q 1/6874* (2013.01); *C12Q 1/6811* (2013.01); *C12Q 1/6869* (2013.01);
(Continued)

(58) Field of Classification Search
CPC ...... C12Q 1/6874; C12Q 1/6869; C12Q 1/68; C12Q 1/00; C12Q 1/6811; G01N 27/3276;
(Continued)

(56) References Cited

U.S. PATENT DOCUMENTS 6,123,819 A   9/2000 Peeters
6,593,666 B1  7/2003 Pinkerton
(Continued)

FOREIGN PATENT DOCUMENTS

WO   WO-2000006770   2/2000
WO   WO-2001057248   8/2001
(Continued)

OTHER PUBLICATIONS

Cui et al., "Nanowire Nanosensors for Highly Sensitive and Selective Detection of Biological and Chemical Species", Science, vol. 293, 2001, pp. 1289-1292.
(Continued)

*Primary Examiner* — Christine T Mui

(57) ABSTRACT

A method for sequencing a nucleic acid template includes forming a nanowire assembly including a semiconductor nanowire and a probe covalently bound to the semiconductor nanowire; contacting the nanowire assembly with a template nucleic acid; contacting the nucleic acid duplexes with an extension nucleic acid, the extension nucleic acid joined to the probe; disrupting the nucleic acid duplexes; and measuring an electrical characteristic of a nanowire assembly of the set of nanowire assemblies.

20 Claims, 6 Drawing Sheets

```
                    ┌─60
                    │     ┌─62
┌───────────────────────────────────────────┐
│  PROVIDE A NANOWIRE ASSEMBLY INCLUDING A   │
│  NANOWIRE COUPLED TO A NUCLEIC ACID ANALYTE│
└───────────────────────────────────────────┘
                    │
                    ▼               ┌─64
┌───────────────────────────────────────────┐
│  CONTACT THE NANOWIRE ASSEMBLY WITH AT LEAST ONE │
│  REAGENT FOR COVALENT MODIFICATION OF NUCLEIC ACIDS│
│         BASED ON NUCLEIC ACID STRUCTURE           │
└───────────────────────────────────────────┘
                    │
                    ▼               ┌─66
┌───────────────────────────────────────────┐
│  MEASURE AN ELECTRICAL CHARACTERISTIC OF THE │
│  NANOWIRE ASSEMBLY TO DETERMINE WHETHER      │
│  OR NOT THE REAGENT PRODUCED A COVALENT      │
│  MODIFICATION OF THE NANOWIRE ASSEMBLY, THEREBY│
│  PROVIDING STRUCTURAL INFORMATION ABOUT       │
│         THE NUCLEIC ACID ANALYTE              │
└───────────────────────────────────────────┘
```

Related U.S. Application Data division of application No. 14/997,669, filed on Jan. 18, 2016, now Pat. No. 9,587,277, which is a continuation of application No. 14/205,283, filed on Mar. 11, 2014, now Pat. No. 9,238,835, which is a continuation of application No. 13/487,638, filed on Jun. 4, 2012, now Pat. No. 8,703,497, which is a continuation of application No. 12/468,831, filed on May 19, 2009, now Pat. No. 8,192,998, which is a continuation of application No. 11/394,147, filed on Mar. 29, 2006, now abandoned.

(60) Provisional application No. 60/666,396, filed on Mar. 29, 2005.

(51) Int. Cl.
  *C12Q 1/6811* (2018.01)
  *C12Q 1/6869* (2018.01)
  *G01N 27/327* (2006.01)
  *C12Q 1/68* (2018.01)

(52) U.S. Cl.
  CPC ..... *G01N 27/3276* (2013.01); *G01N 27/3278* (2013.01); *Y10T 436/14* (2015.01); *Y10T 436/142222* (2015.01); *Y10T 436/143333* (2015.01)

(58) Field of Classification Search
  CPC .. G01N 27/3275; G01N 27/327; G01N 27/30; G01N 27/28; G01N 27/26; Y10T 436/14; Y10T 436/142222; Y10T 436/143333
  USPC .............................................. 506/4; 436/94
  See application file for complete search history.

(56) References Cited

U.S. PATENT DOCUMENTS

| | | |
|---|---|---|
| 6,905,586 B2 | 6/2005 | Lee et al. |
| 7,129,554 B2 | 10/2006 | Lieber et al. |
| 8,192,998 B2 | 6/2012 | Sun et al. |
| 8,703,497 B2 | 4/2014 | Sun et al. |
| 9,238,835 B2 | 1/2016 | Sun et al. |
| 9,587,277 B2 | 3/2017 | Sun et al. |
| 2002/0130311 A1 | 9/2002 | Lieber et al. |
| 2002/0130353 A1 | 9/2002 | Lieber et al. |
| 2003/0022207 A1 | 1/2003 | Balasubramanian et al. |
| 2003/0089899 A1 | 5/2003 | Lieber et al. |
| 2003/0211502 A1 | 11/2003 | Sauer et al. |
| 2003/0215816 A1 | 11/2003 | Sundararajan et al. |
| 2005/0019784 A1 | 1/2005 | Su et al. |
| 2005/0026163 A1 | 2/2005 | Sundararajan et al. |
| 2006/0019247 A1* | 1/2006 | Su .................. C12Q 1/6869 435/6.17 |

FOREIGN PATENT DOCUMENTS

| | | |
|---|---|---|
| WO | WO-2002031183 | 4/2002 |
| WO | WO-2003100096 | 12/2003 |
| WO | WO-2004003535 | 1/2004 |
| WO | WO-2004027093 | 4/2004 |
| WO | WO-2006105360 | 10/2006 |

OTHER PUBLICATIONS

PCT/US2006/011806, Search Report and Written Opinion,., dated Jun. 9, 2006.

Mali et al., "The dnaSET: A Novel Device for Single-Molecule DNA Sequencing", IEEE Transaction on Electron Devices, vol. 51, No. 12, 2004, pp. 2004-2012.

Sakata et al., "DNA Sequencing Based on Intrinsic Molecular Charges", Angewandte Chemie International, vol. 45, No. 14, Mar. 27, 2006, pp. 2225-2228.

\* cited by examiner

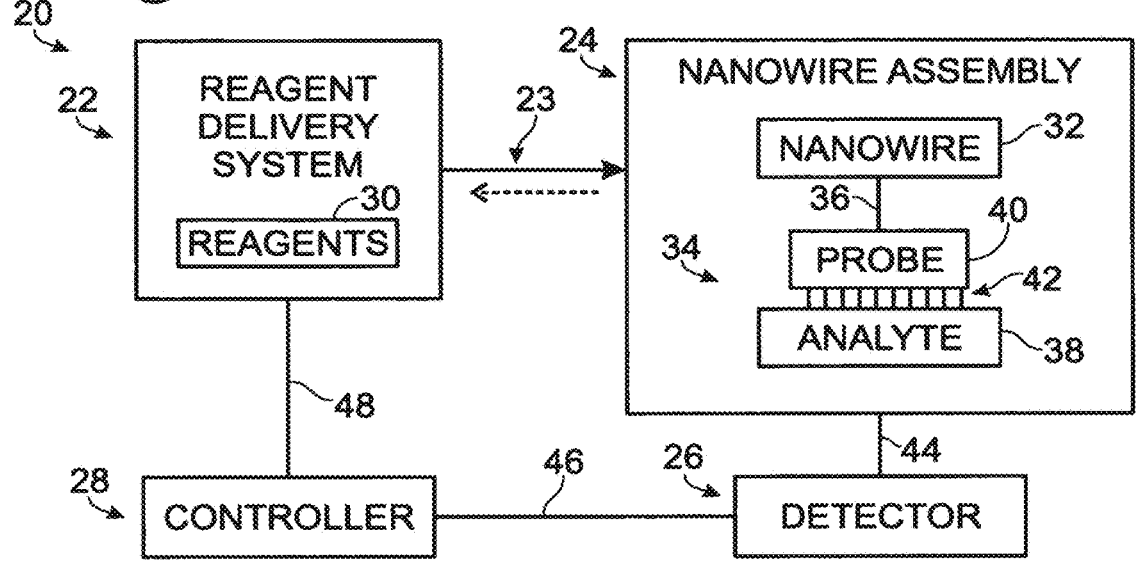
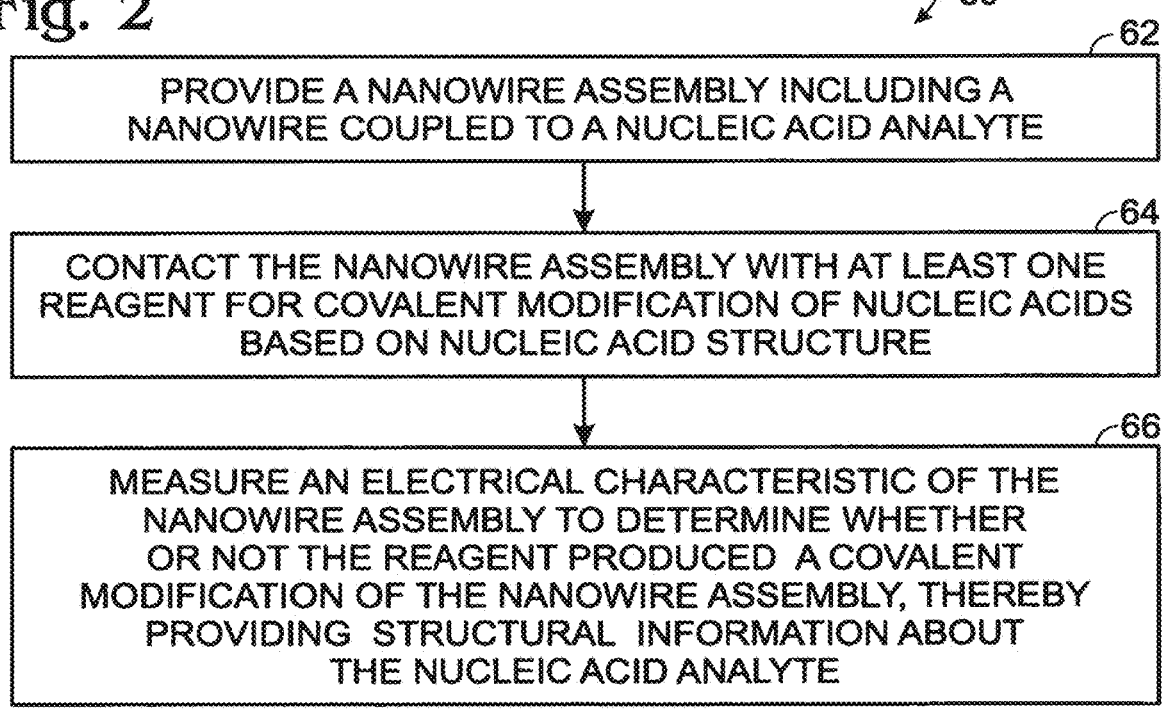

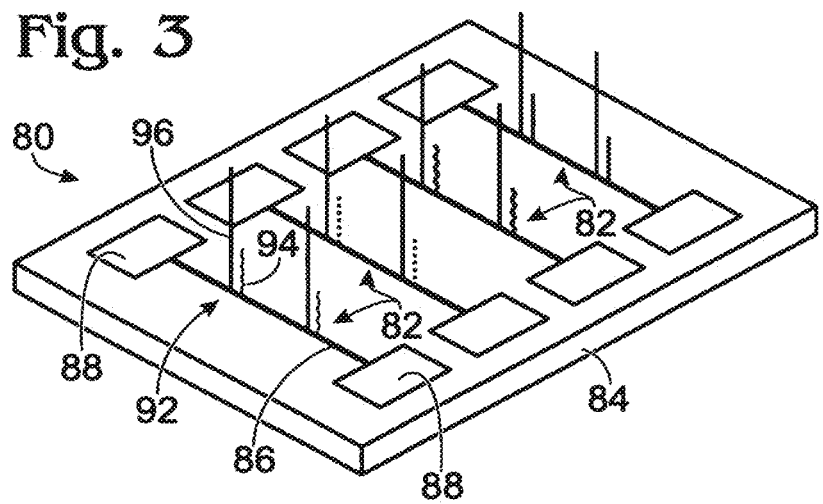
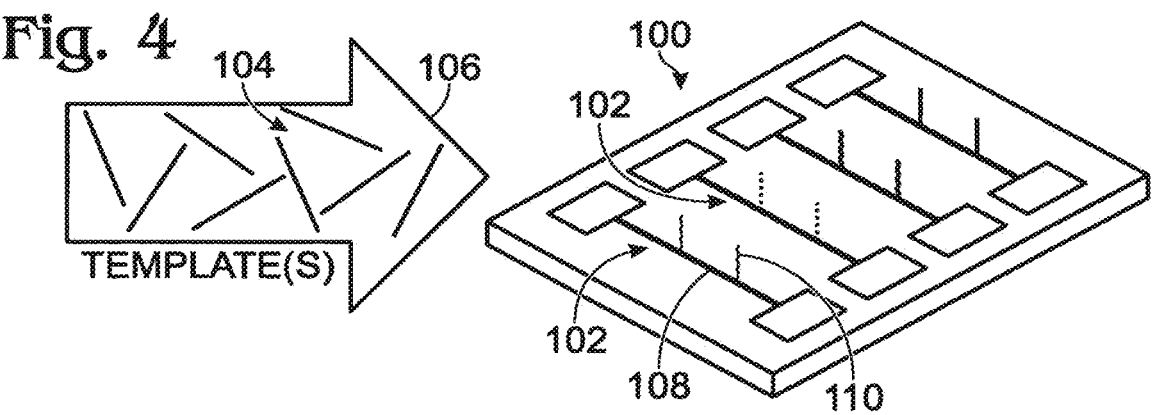
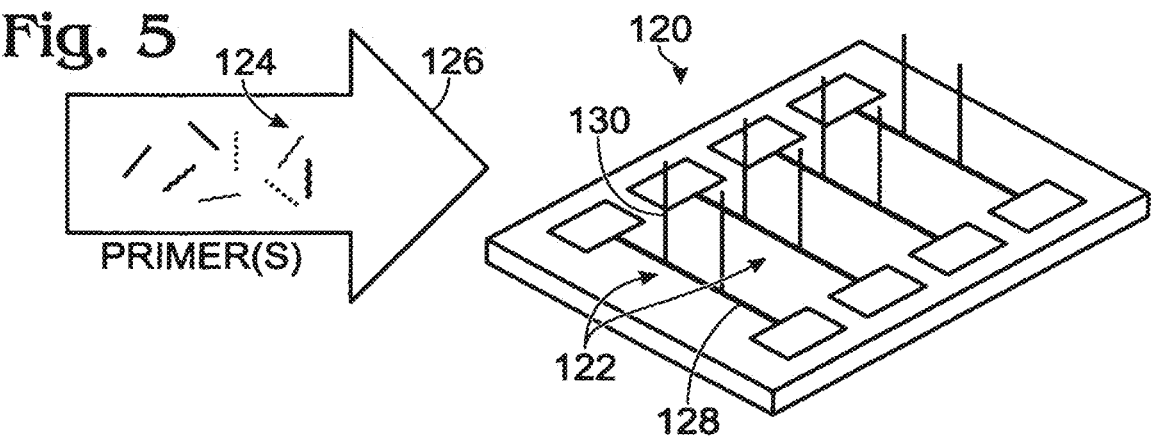

NANOWIRE-BASED SYSTEM FOR ANALYSIS OF NUCLEIC ACIDS

CROSS-REFERENCE TO PRIORITY APPLICATION

This application is a continuation of U.S. application Ser. No. 15/449,889 filed Mar. 3, 2017 (now U.S. Pat. No. 10,415,090), which is division of U.S. application Ser. No. 14/997,669 filed Jan. 18, 2016 (now U.S. Pat. No. 9,587,277), which is a continuation of U.S. application Ser. No. 14/205,283 filed Mar. 11, 2014 (now U.S. Pat. No. 9,238,835), which is a continuation of U.S. application Ser. No. 13/487,638 filed Jun. 4, 2012 (now U.S. Pat. No. 8,703,497), which is a continuation of U.S. application Ser. No. 12/468,831 filed May 19, 2009 (now U.S. Pat. No. 8,192,998), which is a continuation of U.S. application Ser. No. 11/394,147, filed Mar. 29, 2006 (now abandoned), and claims the benefit under 35 U.S.C. § 119(e) of U.S. Provisional Patent Application Ser. No. 60/666,396, filed Mar. 29, 2005, all of which disclosures are herein incorporated by reference in their entirety.

INTRODUCTION

Characterization of nucleic acid sequences has widespread application in a growing number of areas, including clinical diagnostics and therapeutics, forensics, and analysis of bio-terrorism agents, among others. For example, the relatively new field of pharmacogenetics is based on the recognition of a strong genetic component to the effectiveness of medical treatments. In particular, nucleic acid sequence differences between members of the human population can provide much of the variation in response of the population to a medical treatment, such as a drug. Nucleic acid sequence analysis of prospective drug recipients thus can be used to pair each recipient more intelligently with a drug based on the recipient's genetic makeup. However, current sequencing technologies may be limited in their ability to meet the growing demand for sequence information driven by pharmacogenetics and numerous other applications.

SUMMARY

The present teachings provide a system for detection and/or analysis of nucleic acids using nanowires to detect covalent modification of nucleic acids.

BRIEF DESCRIPTION OF THE DRAWINGS

FIG. 1 is a schematic view of an exemplary system for nanowire-based detection and/or analysis of nucleic acids, in accordance with aspects of the present teachings.

FIG. 2 is a flowchart of an exemplary method of nanowire-based analysis of nucleic acids, in accordance with aspects of the present teachings.

FIG. 3 is a somewhat schematic view of an exemplary array of nanowire assemblies that can be included in the systems of the present teachings.

FIG. 4 is a somewhat schematic view of an exemplary approach for coupling templates to nanowires to create an array of nanowire assemblies, in accordance with aspects of the present teachings.

FIG. 5 is a somewhat schematic view of an exemplary approach for coupling primers to nanowires to create an array of nanowire assemblies, in accordance with aspects of the present teachings.

DESCRIPTION OF VARIOUS EMBODIMENTS

Figure 6:
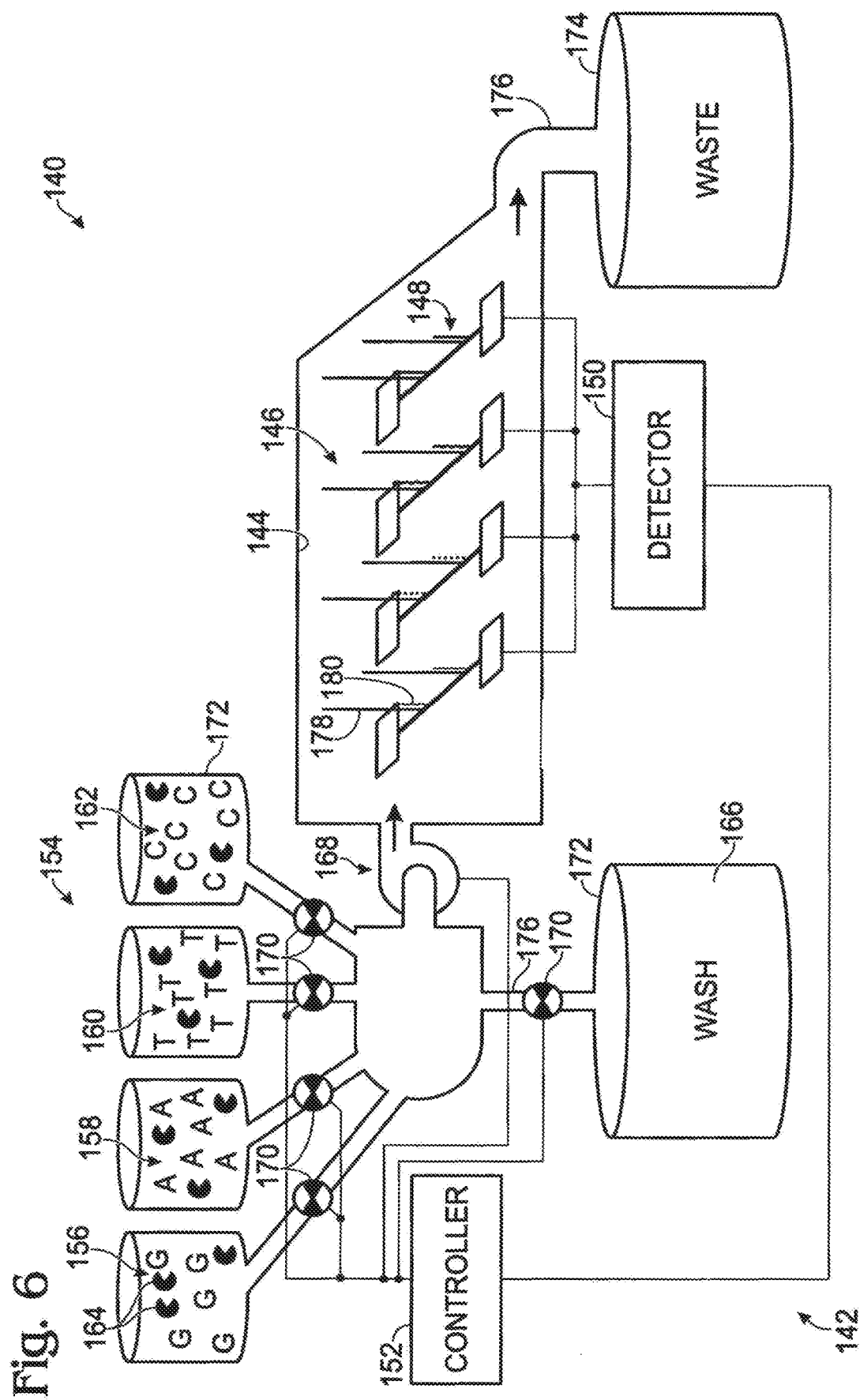
FIG. 6 is a somewhat schematic view of an exemplary system for nanowire-based sequencing of nucleic acids, in accordance with aspects of the present teachings.

The present teachings provide a system for detection and/or analysis of nucleic acids using nanowires to detect covalent modification of nucleic acids. Each nanowire can be coupled to a nucleic acid analyte and a nucleic acid probe base-paired with the analyte, to form a nanowire assembly. The nanowire assembly or any array of nanowire assemblies can be contacted with a reagent for covalent modification of nucleic acids based on nucleic acid structure. For example, the reagent can include a nucleic-acid modifying enzyme, such as a polymerase, a ligase, or a nuclease, among others, capable of lengthening or shortening nucleic acids. A change in the size of a nucleic acid(s) coupled to a nanowire assembly can change the electrical characteristics, such as the conductance, of the nanowire assembly. Accordingly, a detector can be used to measure an electrical characteristic of the nanowire assembly, to determine whether or not the electrical characteristic has been changed by action of the reagent. The presence or absence of change in the electrical characteristic (and/or the size (and/or polarity) of any change) thus can provide structural information, such as sequence information, about the analyte.

Overall, nanowire-based analysis of nucleic acids can have a number of advantages over other systems. These advantages can include increased sensitivity, analysis of smaller amounts of analytes, multiplexed analysis of analytes, performance of a large number of analyses (e.g., hundreds or thousands) in a small space, decreased size of instrumentation, improved portability, and/or the like. For example, in contrast to chain termination approaches to sequencing (e.g., dideoxynucleotide-based sequencing), the nanowire-based systems described herein can sequence nucleic acids by successive primer extension and measurement. Accordingly, the same individual primer and template molecules can be involved in determining the identity of different nucleotides in the template, thereby substantially reducing the number of primer and template molecules necessary for sequencing.

FIG. 1 shows an exemplary system 20 for nanowire-based analysis of nucleic acids. The system can include a reagent delivery system 22, a nanowire assembly 24, a detector 26, and/or a controller 28.

Reagent delivery system 22 can transfer one or more reagents 30 for nucleic acid modification, and particularly fluid reagents, to and/or from the nanowire assembly, shown at 23. The reagent delivery system can be a flow-based system including a pump(s), a valve(s), one or more reservoirs, a channel(s) in which the nanowire assembly is disposed, and/or the like. Further aspects of the reagent delivery system are described, for example, in Section V and in Example 3.

Nanowire assembly 24 can provide a site for nucleic acid modification. In particular, the nanowire assembly can include a nanowire 32 and one or more nucleic acids 34 coupled to the nanowire, shown at 36. The nucleic acids can include an analyte 38, which is the subject of the analysis, and a probe 40, which facilitates structural analysis of the analyte. The probe can be configured to form base pairs with the analyte, shown at 42, so that the probe can couple the analyte to the nanowire, as in the present illustration, or vice versa, among others. In some embodiments, the system can include a plurality of nanowire assemblies, to form an array of nanowires (and nanowire assemblies). Further aspects of nanowires, nanowire arrays, nucleic acids, and coupling nucleic acids to nanowires are described, for example, in Sections I and II and in Examples 1 and 2, among others.

Detector 26 can measure a characteristic such as an electrical characteristic of the nanowire assembly. Accordingly, the detector can be coupled electrically to the nanowire, shown at 44, for example, through a pair of electrodes disposed at spaced positions along the nanowire. In some examples, the detector can measure electrical characteristics from each of a plurality of nanowires disposed in an array, for multiplexed analysis of nucleic acids. Further aspects of detectors are described, for example, in Section IV.

Controller 28 can control various aspects of system operation. For example, the controller can be coupled to the detector, shown at 46, to determine when the detector measures the electrical characteristic and/or on which nanowire assembly of an array. The controller also can store and/or process data received from the detector, such as data corresponding to measured electrical characteristics. The controller also, or alternatively, can be coupled to the reagent delivery system, shown at 48, to control and/or monitor delivery of reagents to/from the nanowire assembly. Further aspects of controllers are described, for example, in Section VI.

FIG. 2 is a flowchart 60 illustrating an exemplary method of nanowire-based analysis of nucleic acids. The method can include steps of (1) providing a nanowire assembly, shown at 62, (2) contacting with nanowire assembly with at least one reagent, shown at 64, and (3) measuring an electrical characteristic of the nanowire assembly, shown at 66. These steps can be performed in any suitable order, in any suitable combination, and any suitable number of times.

A nanowire assembly can be provided. The nanowire assembly can include a nucleic acid analyte coupled to a nanowire, either directly and/or through a nucleic acid probe that pairs (hybridizes) with the analyte. The step of providing can include or be preceded by a step of forming a nanowire assembly. The step of forming a nanowire assembly can include coupling nucleic acids covalently and/or noncovalently to a nanowire. In some examples, an array of nanowire assemblies can be provided. Further aspects of providing and forming a nanowire assembly are described, for example, in Sections I-III and in Examples 1 and 2.

The nanowire assembly can be contacted with a reagent for covalent modification of nucleic acids based on nucleic acid structure. For example, the reagent can include an enzyme (such as a polymerase, ligase, nuclease, etc.) and/or a nucleotide monomer or polymer, among others. A covalent modification can include nucleotide addition to, or removal from, the analyte and/or probe. Accordingly, the structure of the analyte can determine, for example, presence or absence of the covalent modification, the position of the covalent modification (such as position within the analyte and/or probe), and/or the extent of the covalent modification (such as number of nucleotides added or removed). Further aspects of reagents and covalent modification of nucleic acids are described, for example, in Section V and in Examples 3-5, among others.

An electrical characteristic of the nanowire assembly can be measured. The electrical characteristic, and particularly a change in the electrical characteristic, if any, can be used to determine whether or not the analyte has a structure that allows covalent modification by the reagent, thus providing information about the analyte's structure. Further aspects of measuring electrical characteristics and determining analyte structure based on changes in an electrical characteristic are described, for example, in Section IV and in Examples, 3-5, among others.

The steps of contacting and measuring can be repeated any suitable number of times. In some examples, contacting and measuring can be repeated with different reagents (such as different enzymes and/or nucleotide substrates) and/or can be repeated cyclically with the same substrate multiple times, such as for determining the sequence of an analyte region of two or more nucleotides.

The methods of the present teachings also or alternatively can include a step of adjusting the stringency of base-pair interactions. The stringency can be adjusted to alter the stability of nucleic acid strand-strand interactions, such as to increase or decrease the total number, uninterrupted length, and/or type of base-pair interactions (e.g., G-C base pairs are generally more stable than A-T base pairs) necessary to hold together nucleic acid strands that are complementary. In some examples, adjusting the stringency can include disrupting base-pair interactions of nucleic acid duplexes, such that only less stable duplexes and/or at least substantially all double-stranded duplexes are disrupted to form unpaired single strands. Adjusting stringency can be performed electrically (e.g., by positively or negatively biasing a nanowire assembly), by changing the temperature of the nanowire assembly (e.g., by heating or cooling a corresponding reaction compartment and/or fluid disposed in, or destined for, the compartment), and/or chemically (e.g., by adjusting ionic strength, the concentration of divalent or multivalent cations and/or anions, the solvent dielectric constant (e.g., by changing the concentration of dimethylformamide or another organic solvent), and/or enzymatically (e.g., by adding or adjusting the concentration of enzymes such as helicase that favor the pairing or unpairing of nucleic acid bases or strands), and/or changing the concentration of chaotropic agents (such as urea), among others). Nucleic acid duplexes can be disrupted, for example, after contacting and before measuring (e.g., to remove a contribution to the electrical characteristic produced by nucleic acid duplexes), or after contacting and after measuring (e.g., to facilitate performance of another cycle of contacting and measuring). In some examples, adjusting the stringency can include reducing the ionic strength of fluid in contact with the nanowire assembly to increase the sensitivity of measuring the electrical characteristic.

Further aspects of the present teachings are described in the following sections, including (I) nanowires; (II) nucleic acids, including (A) analytes and (B) probes; (III) nanowire assemblies; (IV) detectors; (V) reagent delivery systems; (VI) controllers; and (VII) examples.

I. Nanowires

The systems of the present teachings include one or more nanowires. A nanowire, as used herein, is an elongate semiconductor having a sub-micrometer cross-sectional dimension at one or more (or all) positions along its length. The cross-sectional dimension (and/or orthogonal cross-sectional dimensions) can be less than about 500 nm, 100 nm, 20 nm, 5 nm, or 1 nm, among others.

The nanowires can have any suitable length. Exemplary lengths include at least about 1 µm, 5 µm, or 20 µm, among others. Furthermore, the nanowires can have any suitable aspect ratio (length relative to a cross-sectional dimension (and/or relative to orthogonal cross-sectional dimensions) to produce an elongate structure. Exemplary aspect ratios include at least about 2:1, 10:1, 100:1, or 1000:1.

The nanowires can have any suitable cross-sectional shape. Exemplary cross-sectional shapes include circular, elliptical, polygonal (triangular, rectangular, etc.), irregular, and/or a combination thereof. In some examples the nanowires can be nanotubes having a hollow core.

The nanowires can be formed of any suitable material(s). For example, the nanowires can be formed of semiconductor materials (elements or alloys), with or without a dopant. Exemplary semiconductor materials to form the body (or a coating or lining) of the nanowire include silicon, germanium, and/or carbon, among others. Exemplary dopants include n-type dopants and/or p-type dopants, such as nitrogen and phosphorus, respectively, among others. Other materials that can be suitable to form the body (and/or coating or lining) of the nanowires or as dopants therein are described in the following patent applications, which are incorporated herein by reference: Ser. No. 09/935,776, filed Aug. 22, 2001 (Pub. No. US 2002/0130311 A1); Ser. No. 10/020,004, filed Dec. 11, 2001 (Pub. No. US 2002/0117659 A1); Ser. No. 10/033,369, filed Oct. 24, 2001 (Pub. No. US 2002/0130353); and Ser. No. 10/196,337, filed Jul. 16, 2002 (Pub. No. US 2003/0089899 A1).

II. Nucleic Acids

The systems of the present teachings provide nanowires coupled to nucleic acids. A nucleic acid (or an oligonucleotide, an oligomer, or a polynucleotide), as used herein, is a polymer of at least two nucleotide subunits linked together. The nucleic acid can be single-stranded or double-stranded (a duplex), among others. Double-stranded nucleic acids generally are formed by hydrogen-bonding (base-pairing) between aligned nucleotides of paired strands of nucleic acids, for example, adenosine (A) paired with thymidine (T) (or uridine (U) in RNA), and guanosine (G) paired with cytidine (C), among others.

The nucleic acid can have any suitable natural and/or artificial structure. The nucleic acid can include a sugar-phosphate backbone of alternating sugar and phosphate moieties, with a nucleotide base attached to each sugar moiety. Any sugar(s) can be included in the backbone including ribose (for RNA), deoxyribose (for DNA), arab- inose, hexose, 2'-fluororibose, and/or a structural analog of a sugar, among others. The nucleotide base can include, for example, adenine, cytosine, guanine, thymine, uracil, inosine, 2-amino adenine, 2-thiothymine, 3-methyl adenine, C5-bromouracil, C5-fluorouracil, C5-iodouracil, C5-methyl cytosine, 7-deazaadeine, 7-deazaguanine, 8-oxoadenine, 8-oxoguanine, 2-thiocytosine, or the like. The nucleic acids of the present teachings can include any other suitable alternative backbone. Exemplary alternative backbones include phosphoramides, phosphorothiozates, phosphorodithioates, O-methylphosphoroamidites, peptide nucleic acids, positively charged backbones, non-ribose backbones, etc. Nucleic acids with artificial backbones and/or moieties can be suitable, for example, to increase or reduce the total charge, increase or reduce base-pairing stability, increase or reduce chemical stability, to alter the ability to be acted on by a reagent, and/or the like.

A nanowire can be coupled to a nucleic acid analyte (or a plurality of structurally different analytes) and/or to a nucleic acid probe (or a plurality of structurally different probes). Furthermore, the nanowire can be coupled to a single molecule or to a plurality of molecules of each analyte and/or probe.

A. Analytes

An analyte, as used herein, is a nucleic acid that is the subject of a nanowire-based analysis. The analyte can be from any suitable source, can have any suitable structure, and can be analyzed for any suitable feature. In some examples, the analyte can be a template, that is, a nucleic acid used as a model or guide for forming at least a region of another nucleic acid. The template can, for example, direct addition of one or more nucleotides to a probe, serially or in parallel, according to a complementary region of the template that base-pairs with the one or more nucleotides.

The analyte can be from any suitable source. Exemplary sources can include a human subject, a nonhuman animal, a plant, a microorganism, a research sample, an environmental sample (such as soil, air, water, etc.), and/or in vitro synthesis, among others.

The human subject can be a disease patient, a genetic screening subject, a person to be identified, a forensic subject, and/or the like. The analyte can be obtained from any suitable site in the human subject, including a sample from blood, plasma, serum, sperm, urine, sweat, tears, sputum, mucus, milk, a tissue sample, a tumor biopsy, cultured cells, and/or the like.

The analyte can be obtained in any suitable form by any suitable processing. For example, the analyte can be included in a crude lysate or can be a purified analyte obtained, for example, by ion exchange chromatography, selective precipitation, centrifugation, and/or amplification (such as with the polymerase chain reaction), among others. The analyte can be single- or double-stranded and can have any suitable size. In some examples, the analyte can have a single size or a set of sizes produced by shearing, restriction endonuclease digestion, in vitro synthesis, amplification, limited chemical digestion, and/or the like. In some examples, the analyte coupled to a nanowire includes a plurality of discrete strands of similar or identical length and sequence content, or of distinct lengths and/or sequence content. Strands of distinct length can be overlapping fragments, for example, including a common region of similar or identical sequence, such as for hybridization (base-pairing) with a probe. The analyte can be any suitable size relative to the probe. In some examples, the analyte is about the same size as the probe. In some examples, the analyte is longer than the probe and can be substantially longer than the probe, such as at least about two, ten, or one hundred times as long.

The analyte can be analyzed to obtain structural information about any suitable feature(s). Generally, the structural information relates to a sequence feature. The sequence feature can be defined by any suitable length of nucleotides. The structural information thus can be the presence or absence of a sequence feature of interest, the nucleotide identity (e.g., G, A, T, or C) at a particular position(s) within the analyte (e.g., to characterize a single nucleotide corresponding to a single nucleotide polymorphism in the population), and/or the particular sequence of a stretch of at least about 5, 10, 50, 200, or 1000 nucleotides, among others, of the analyte. The sequence feature thus can be compared to a known sequence, to look for nucleotide identity and/or differences, or can correspond to a previously unsequenced region of a genome or other polynucleotide structure.

B. Probes

A probe, as used herein, is a nucleic acid that facilitates analysis of the nucleic acid analyte. The probe can be from any suitable source, can have any suitable structure, and can be used to analyze the analyte for any suitable feature(s).

The probe can be obtained from a natural and/or artificial source. Accordingly, the probe can be synthesized or formed by a cell(s), a cell lysate(s), a synthetic enzyme(s), chemical synthesis, enzymatic cleavage, chemical cleavage, and/or ligation, among others. The probe thus can be RNA, DNA, or any suitable artificial derivative thereof. Furthermore, the probe can belong to the same structural class of molecules as the analyte (e.g., each being DNA or each being RNA) or to a different class of molecules (e.g., the probe being DNA and the analyte RNA (or vice versa), or the probe having an uncharged or positively charged backbone and the analyte having a phosphodiester backbone, among others).

The probe can have any suitable structure relative to the analyte. The probe can be configured to form a duplex with the analyte through base-pair interactions, so that the probe and analyte together form an at least partially double-stranded nucleic acid. Accordingly, a section (or all) of the probe can be complementary to a section (or all) of the analyte. Alternatively, or in addition, the probe can include a double-stranded region, independent of the analyte, for example, to couple the probe to a nanowire. The probe can be configured to hybridize (base-pair) to any region of the analyte, for example, the probe can hybridize adjacent an end or spaced from the end of the analyte. In some examples, the probe can be a primer. The primer can be configured so that the 3'-end of the probe is base-paired with the analyte and spaced from the ends of the analyte, allowing the 3'-end to be extended with a polymerase (or ligase) and a suitable nucleotide substrate(s). The probe can have any suitable length sufficient to form a duplex structure with another nucleic acid, particularly the analyte. The duplex structure can be stabilized, for example, by nucleotide addition to the probe (such as with a polymerase or ligase, among others).

The systems of the present teachings can include one probe or a plurality of probes. The plurality of probes can be configured to form duplexes with different analytes, different regions of the same analyte, or with the same region of the same analyte (e.g., see Example 4).

III. Nanowire Assemblies

The systems of the present teachings can include one or more nanowire assemblies. The nanowire assemblies can be disposed in any suitable arrangement, can include any suitable number and type of nucleic acids, and can couple the nucleic acids to nanowires by any suitable mechanism(s).

The systems of the present teachings can include an array of nanowire assemblies. The nanowire assemblies can be arrayed in a linear arrangement, a two-dimensional arrangement, and/or a three-dimensional arrangement (such as stacked two-dimensional arrays). The array can include any suitable number of assemblies, including at least about ten, one-hundred, or one-thousand, among others. The nanowire assemblies can include a different probe (or probes) or the same probe (or probes) in each assembly, and/or a different analyte (or analytes) or the same analyte(s) or analyte region(s) in each assembly. Accordingly, the nanowire assemblies can be configured to analyze distinct regions (nonoverlapping or overlapping) of the same analyte, the same region of the same analyte, and/or different regions of different analytes.

The analyte and probe can be coupled to each nanowire by any suitable mechanism. The analyte and/or the probe can be coupled directly to the nanowire by a covalent or noncovalent mechanism. Covalent mechanisms include bond formation between any suitable reactive pair with pair members disposed on the nanowire and a nucleic acid. An exemplary mechanism includes reaction of 1-ethyl-3-(3-dimethylaminopropyl)-carbodiimide hydrochloride (EDC) with nucleic acids to form nucleic acid derivatives that can react with activated nanowire surfaces. Alternatively, or in addition, nucleic acids can be bound to nanowires through noncovalent specific binding pair interactions. For example, a first member of a specific binding pair can be attached to a nanowire and a second member of the specific binding pair can be attached (or included in) a nucleic acid analyte and/or probe. Specific binding pairs generally undergo specific binding, that is, binding to one another to the exclusion of binding to most other moieties. Specific binding can be characterized by a dissociation constant or coefficient (alternatively termed an affinity or binding constant or coefficient). Generally, dissociation constants for specific binding range from $10^{-4}$ M to $10^{-12}$ M and lower, and preferred dissociation constants for specific binding range from $10^{-8}$ or $10^{-9}$ M to $10^{-12}$ M and lower. Exemplary specific binding pairs are presented in Table 1:

TABLE 1

Exemplary Specific Binding Pairs

| Specific Binding Member | Partner |
|---|---|
| cell-surface receptor | secreted hormone or cell-associated ligand |
| nuclear receptor | nuclear hormone or DNA |
| antibody | antigen |
| avidin or streptavidin | biotin |
| lectin or carbohydrate receptor | carbohydrate |
| DNA | antisense DNA; protein |
| RNA | antisense or other RNA; protein |
| enzyme | enzyme substrate or regulator |
| histidine | NTA (nitrilotriacetic acid) |
| IgG | protein A or protein G |

Specific binding pair interactions (e.g., base pairing) also can be used to associate the analyte and probe with each other. Accordingly, the probe (or analyte) can be coupled more directly to the nanowire than the analyte (or probe) with which it is base paired. Moreover, the probe and analyte can be coupled to a nanowire at the same time (e.g., in a base-paired condition) or sequentially, for example, by coupling the probe first and then the analyte, or vice versa (see Example 2). Furthermore, the probe and/or analyte can be coupled to the nanowire at a single site or at multiple sites (e.g., spaced sites) along each molecule of the probe/analyte (see Example 6).

Probes and/or analytes can contact nanowires to form nanowire assemblies at any suitable time using any suitable contact mechanism. In some examples, the nanowires can be disposed in an array and then different probes and/or analytes selectively contacted with (and coupled to) individual nanowires or subsets of nanowires in the array. For example, individual probes and/or analytes (or different sets thereof) can be selectively dispensed to regions of the array in small droplets of fluid so that the regions remain in fluid isolation, such as by inkjet printing technology (e.g., using a dispensing head with thin-film heater elements and/or piezoelectric elements, among others, as used in inkjet printheads). Alternatively, or in addition, the array of nanowires can be contacted with the probes and/or analytes with the nanowires disposed in fluid communication. For example, the probes and/or analytes can selectively interact with the nanowires based on specific binding partners (and particularly nucleic acids) previously coupled to the nanowires.

Further aspects of nanowires, nanowire assemblies, and assays that may be performed with nanowires are described in the following patent applications, which are incorporated herein by reference: U.S. Provisional Patent Application Ser. No. 60/612,315; U.S. patent application Ser. No. 09/935,776, filed Aug. 22, 2001 (Pub. No. US 2002/0130311 A1); U.S. patent application Ser. No. 10/020,004, filed Dec. 11, 2001 (Pub. No. US 2002/0117659 A1); U.S. patent application Ser. No. 10/033,369, filed Oct. 24, 2001 (Pub. No. US 2002/0130353); and U.S. patent application Ser. No. 10/196,337, filed Jul. 16, 2002 (Pub. No. US 2003/0089899 A1).

IV. Detectors

The systems of the present teachings generally include one or more detectors (also termed sensors) to measure an electrical characteristic of each nanowire (and nanowire assembly) of a nanowire array. In some examples, the detector is coupled electrically to each nanowire in a serial fashion, using, for example, electronic switching devices. Accordingly, the detector can be coupled to the nanowires in a repeatable cycle, and the electrical characteristic of each nanowire can be detected periodically to measure any time-dependent (and generally reagent-dependent) changes (if any) in the electrical characteristic.

The detector can measure any suitable electrical characteristic. Exemplary electrical characteristics include conductance, resistance, current, voltage, and/or the like. The electrical characteristic can be measured qualitatively (e.g., change or no change and/or a positive or negative change) or quantitatively (e.g., to determine a magnitude of the change, if any). The electrical characteristic can provide an analog and/or digital output.

V. Reagent Delivery Systems

The systems of the present teachings can include one or more reagent delivery systems. The reagent delivery systems can include one or more pumps, valves, fluid reservoirs, channels, and/or reagents, among others.

Pumps generally include any mechanism for moving fluid and/or reagents disposed in fluid. In some examples, the pump can be configured to move fluid and/or reagents through passages with small volumes (i.e., microfluidic structures). The pump can operate mechanically by exerting a positive or negative pressure on fluid and/or on a structure carrying fluid, electrically by appropriate application of an electric field(s), or both, among others. Exemplary mechanical pumps may include syringe pumps, peristaltic pumps, rotary pumps, pressurized gas, pipettors, etc. The mechanical pumps may be micromachined, molded, etc. An exemplary peristaltic pump created with a fluidic layer and a control layer that are elastomeric is described, for example, in U.S. Pat. No. 6,408,878, issued Jun. 25, 2002, which is incorporated herein by reference. Exemplary electrical pumps can include electrodes and may operate by electrophoresis, electroendoosmosis, electrocapillarity, dielectrophoresis (including traveling wave forms thereof), and/or the like.

Valves generally include any mechanism for regulating the passage of fluid through a channel. The valves can include, for example, deformable members that can be selectively deformed to partially or completely close a channel, a movable projection that can be selectively extended into the channel to partially or completely block the channel, an electrocapillary structure, and/or the like. The valves can be operable, for example, to select a reagent to be contacted with a nanowire assembly (or assemblies), from a set of available reagents. Accordingly, the valves can be operable to provide selective fluid communication between a nanowire assembly (or assemblies) in a channel (a reaction compartment) and two or more reagent reservoirs.

Fluid reservoirs generally include any compartments for holding reagents before and/or after they have passed through the reaction compartment holding one or more nanowire assemblies. The fluid reservoirs can have any suitable volume. In some examples, the fluid reservoirs have a volume that is substantially larger than the volume of the reaction compartment, such as a volume that is at least about ten-fold, one-hundred-fold, or one-thousand fold the reaction compartment volume. The fluid reservoirs can be configured to be accessible from outside the system, to facilitate adding or removing fluid, such as with a pipette.

Channels generally include any passages that allow flow of fluid and/or movement of reagents. The channels can extend, for example, between fluid reservoirs of the system, and can define a reaction compartment that holds the nanowire assembly (or assemblies). The channels can have any suitable dimensions. In some embodiments, the channels can be microfluidic channels. Microfluidic channels or compartments, as used herein, can have a cross-sectional dimension, at one or more positions along their length, of less than about one micrometer or less than about 100 nanometers.

Reagents can have any suitable function in nucleic acid analysis. The reagents can be configured, for example, to structurally modify nucleic acids of nanowire assemblies, to wash out (remove) a previously dispensed reagent and/or a released nucleic acid, to adjust the stringency of hybridization between paired nucleic acid strands, to disrupt base-pair interactions (denature duplexes into single strands) substantially or completely, and/or the like.

Reagents include any chemical substances that can contact nanowire assemblies to facilitate analysis of nucleic acids. The chemical substances can be present in any suitable form in a reagent, including as a mixture, a complex, a solution, a suspension, and/or the like. Exemplary reagents can include catalysts and/or mono- and/or polynucleotides. Other exemplary reagent components can include carrier fluids (such as water and/or an organic fluid), enzyme cofactors (such as divalent cations (e.g., magnesium, zinc, manganese, etc.), ribonucleoside triphosphates (such as adenosine triphosphate (ATP)), S-adenosyl methionine (SAM), etc.), reducing agents (such as dithiothreitol (DTT), beta-mercaptoethanol, etc.), salts (e.g., to adjust ionic strength), stabilizing agents (such as serum albumin (e.g., BSA), size-based exclusion polymers (such as polyethylene glycol (PEG)), and/or the like.

Catalysts can include any material that can increase the rate of a chemical reaction (particularly a reaction that modifies nucleic acids) without being consumed or produced by the reaction. Exemplary catalysts for nucleic acid modification are proteins (enzymes). Any suitable enzymes can be included in reagents. Exemplary enzymes can add single nucleotides or polynucleotides covalently to a nucleic acid, generally based on the sequence of a partner strand based-paired with the nucleic acid (i.e., templated addition). Single-nucleotide addition enzymes, which add individual nucleotides successively, generally include polymerases, such as DNA polymerases (e.g., DNA Polymerase I (or fragments/derivatives thereof (such as the Klenow fragment)), thermostable DNA polymerases (such as Taq Polymerase, Vent Polymerase, Pfu Polymerase, etc.), and/or the like), RNA polymerases (such as phage-derived polymerases (such as SP6, T7, or T3 RNA polymerase), reverse transcriptases that add deoxyribonucleotides based on an RNA template, and/or the like. Polynucleotide addition enzymes, which add two or more nucleotides at the same time to a nucleic acid, can include ligases (such as T4 DNA ligase, Taq DNA Ligase, *E. coli* DNA Ligase, etc.). Other exemplary enzymes can include nucleases (cleavage enzymes), such as restriction enzymes, ribonucleases or deoxyribonucleases (e.g., single- or double-strand specific enzymes), and/or the like. Other exemplary catalysts can include polynucleotides (e.g., RNA), synthetic polymers, transition metal complexes, reactive surfaces, etc.

The reagents can include one or more mono- or polynucleotides for contact with nanowire assemblies. Mononucleotide reagents can include, for example, nucleoside triphosphates, including deoxyribonucleoside triphosphates (dNTPs) (e.g., dATP, dCTP, dGTP, dTTP, etc.), ribonucleoside triphosphates (NTPs) (e.g., ATP, CTP, GTP, UTP, etc.), and/or mixtures thereof, among others. Polynucleotide reagents can include, for example, nucleic acid dimers, trimers, tetramers, etc. The polynucleotide reagents can be configured to be partially or completely complementary to a region of the analyte (or to a region being tested for its presence or absence in the analyte). In some examples, the polynucleotide reagents can include a 5'-phosphate for ligation to a 3'-hydroxyl of a probe.

VI. Controllers

The systems of the present teachings can include at least one controller. The controller can interface with (control, coordinate, and/or record) various portions of the systems. For example, the controller can interface with operation of the reagent delivery system and/or the detector, among others.

The controller can interface with any suitable aspect of the reagent delivery system. In some examples, the controller can control operation of the pump(s), such as determining when the pump is operated, the rate of pump operation, selection of a subset of pumps that are operated, etc. Alternatively, or in addition, the controller can control operation of valves, to determine, for example, which reagent(s) are selected for addition to a reaction compartment, in what order, at what rate, and/or for how long, among others. The controller also can receive inputs from a user for user preferences related to operation of the pumps and/or valves, and/or can store and/or report data related to aspects of reagent delivery.

The controller can interface with any suitable aspects of the detector(s). In some examples, the controller can control operation of the detector(s), such as determining when the detector is operated and/or which nanowire assembly is electrically coupled to the detector at a given time and/or in what order, the size and timing of a back gate voltage applied to a substrate supporting a nanowire assembly (or assemblies), a voltage and/or current applied to the nanowire assembly, and/or the like. The controller also can receive inputs from a user for user preferences related to operation of the detector(s), and/or can collect, store, and/or report data related to aspects of detection.

VII. Examples

The following examples describe selected aspects and embodiments of systems for nanowire-based analysis of nucleic acids. These examples are included for illustration and are not intended to limit or define the entire scope of the present teachings.

Example 1. Nanowire Arrays

This example describes an exemplary array of nanowire assemblies; see FIG. 3.

Nanowire array 80 can include a plurality of nanowire assemblies 82 supported by a substrate 84. The nanowire assemblies can be disposed in a linear array on the substrate, as shown here, and/or in a two- (or three-) dimensional array.

Each nanowire assembly can include a nanowire 86 extending between spaced electrodes 88. The nanowire can be electrically coupled to the electrodes, so that current can pass between the electrodes through the nanowire. Exemplary electrodes can be formed of an electrically conductive material, generally a conductive metal(s) or metal alloy. In exemplary embodiments, the electrodes can be formed of gold. Electrodes can be formed on the substrate before or after placement of the nanowires. In exemplary embodiments, the electrodes can be formed by photolithography and/or ion beam lithography.

The substrate can have any suitable composition and structure. In some embodiments, the substrate can be generally planar, and can include an electrical insulator layer (such as silicon dioxide) disposed over a semiconductor layer (such as silicon). The semiconductor layer can be used to apply a back gate voltage when the nanowire assembly functions as a field effect transistor (FET), with the electrodes acting as source and drain.

Each nanowire assembly can include nucleic acids 92 coupled to a nanowire. The nucleic acids can include a probe 94 (such as a primer) and an analyte 96 (such as a template) base-paired with the probe. The assemblies (or subsets of two or more of the assemblies) can include the same probe or can include different probes, as shown in the present illustration. The assemblies (or subsets of two or more of the assemblies) can include the same analyte (or analyte region), as shown in the present illustration, or different analytes.

Example 2. Coupling Nucleic Acids to Nanowires

This example describes exemplary approaches for coupling nucleic acids to nanowires; see FIGS. 4 and 5.

FIG. 4 shows an exemplary array 100 of nanowire assemblies 102 prepared to receive template 104, shown by the arrow at 106. Each nanowire assembly can include a nanowire 108 and a different probe 110 coupled to the nanowire. The probes can be coupled to the nanowires before or after they are disposed in the array. Templates 104 can be placed in contact with the array and allowed to hybridize with the probes and/or can be coupled directly to the nanowires. Accordingly, the probes can be configured to select complementary templates from a nucleic acid mixture of templates and nontemplate species. After hybridization, unpaired templates (and nontemplate species) can be removed.

FIG. 5 shows an exemplary array 120 of nanowire assemblies 122 prepared to receive primers 124, shown by the arrow at 126. Each nanowire assembly can include a nanowire 128 and a different (or the same) template 130 coupled to the nanowire. The templates can be coupled to the nanowires before or after the nanowires are disposed in the array. Primers 124 can be placed in contact with the array and allowed to hybridize with the templates and/or can couple directly to the nanowires. Accordingly, the templates can be configured to select complementary primers from a primer mixture. After hybridization, unpaired (e.g., excess) primer molecules can be removed.

Example 3. System for Nanowire-based Sequencing

Figure 7:
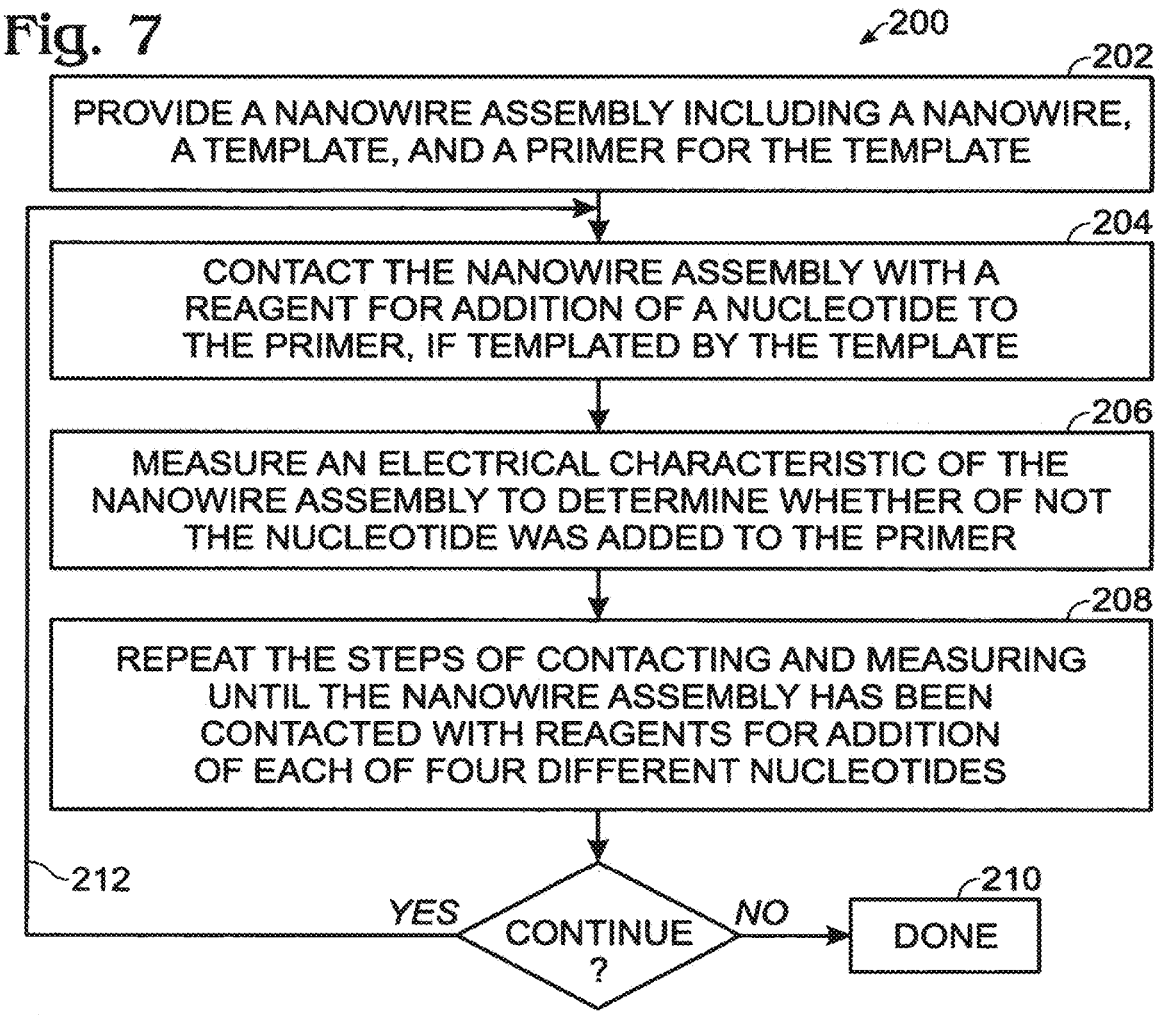
FIG. 7 is a flowchart of an exemplary method of nanowire-based sequencing of nucleic acids, in accordance with aspects of the present teachings.
Figure 8:
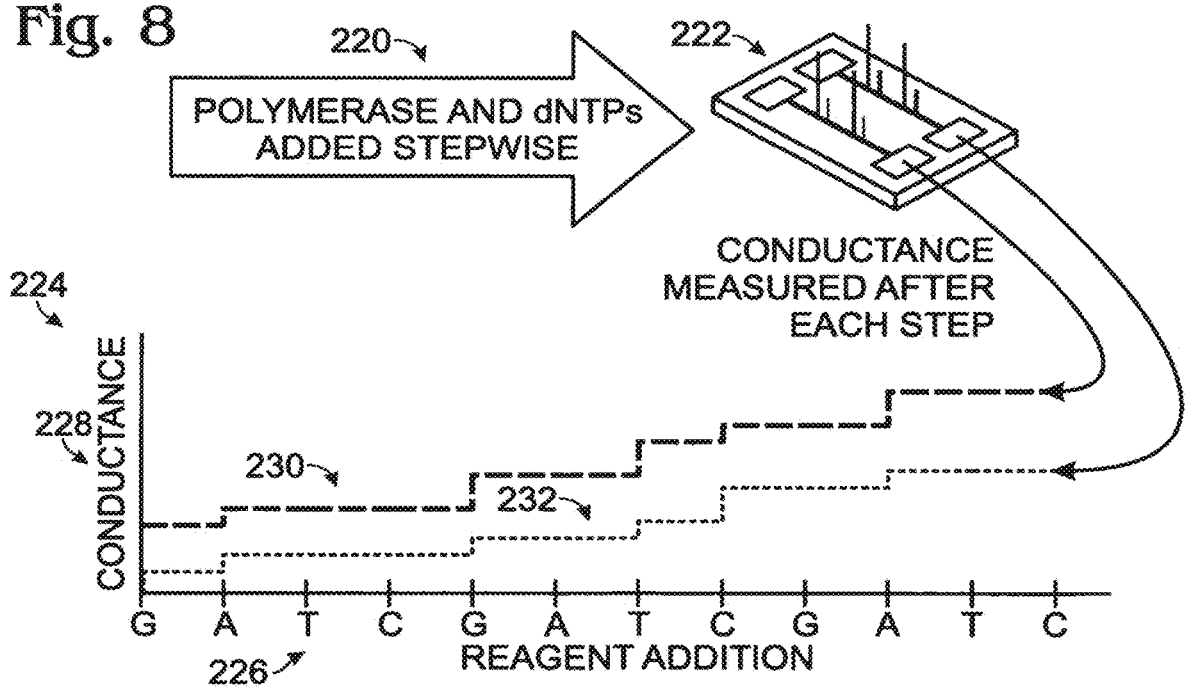
FIG. 8 is a somewhat schematic view of an exemplary approach to sequencing nucleic acids using an array of nanowire assemblies and of a graph of exemplary data that may be obtained with this approach, in accordance with aspects of the present teachings.

This example describes an exemplary system, including apparatus, method, and data, for nanowire-based sequencing; see FIGS. 6-8.

A system 140 for nanowire based sequencing can include a reagent delivery system 142 in fluid communication with a reaction compartment 144 holding an array 146 of nanowire assemblies 148. The system also can include a detector 150 electrically coupled (or couplable) to the array of nanowire assemblies, and a controller 152 in communication with the detector and the reagent delivery system.

Reagent delivery system 142 is configured to move fluid through reaction compartment 144 for contact with array 146. The reagent delivery system thus can include a plurality of fluid reagents 154 for covalent modification of nucleic acids, such as four different nucleoside triphosphates (dNTPs) 156, 158, 160, and 162, each disposed in an aqueous solution with DNA polymerase molecules 164. The fluid reagents also can include a wash reagent 166, which can be used, for example, to wash dNTP reagents out of the reaction compartment after they have contacted the nanowire assemblies. Movement of the fluid reagents can be driven by a pump 168 disposed, for example, downstream of the fluid reagents. The pump can drive each fluid reagent to (and past) the reaction compartment. Fluid reagents can be selected according to selective opening and closing of valves 170 disposed between reagent reservoirs 172 and the reaction compartment. The reagent delivery system can define a plurality of compartments for holding fluid, including the reagent reservoirs, the reaction compartment, a waste reservoir 174 disposed downstream of the reaction compartment, and channels 176 extending between and/or defining these structures. In some examples, the reagent delivery system can be disposed on a planar substrate, with microfluidic (or larger) passages for holding and carrying fluid formed on and/or above the planar substrate by a fluidics layer abutted to the substrate.

Nanowire array 146 can include nanowire assemblies each coupled to nucleic acids corresponding to a template 178 base-paired with a primer 180. In operation, the nucleotide addition reagents 156-162 can be individually dispensed to the reaction compartment. Before, during, and/or after each addition, the detector can measure the conductance of each nanowire assembly, allowing a determination of whether or not each nucleotide was attached to the primer based on the sequence of the template, and, if added, how many subunits were attached.

FIG. 7 shows an exemplary method 200 of sequencing nucleic acid templates, which can be performed with the sequencing system shown in FIG. 6. The method can include a step of providing a nanowire assembly, shown at 202. The nanowire assembly can include a nanowire, a template, and a primer for the template. The nanowire assembly can be part of an array of assemblies. The method can include a step of contacting the nanowire assembly with a nucleotide addition reagent, shown at 204. The nucleotide addition reagent can include, for example, a polymerase and nucleoside triphosphate. The method can include a step of measuring, shown at 206. Measuring can detect an electrical characteristic of each nanowire assembly before, during, and/or after the step of contacting to determine whether or not one or more nucleotides were attached (covalently) to each nanowire assembly. The steps of contacting and measuring can be repeated for the other nucleotide reagents (or only a subset thereof), shown at 208. In some examples, the steps can be repeated until each of the four different nucleotide reagents (or a suitable subset thereof, such as two different nucleotide reagents corresponding to two known single nucleotide polymorphisms) have separately contacted the nanowire assemblies. If only a single nucleotide position of the template, immediately adjacent the end of the primer, is of interest, the method can be terminated, shown at 210. However, if the controller determines that the template can and/or should be sequenced more, to obtain sequence information about additional nucleotide positions in the template, the steps of contacting, measuring, and repeating can be performed again, shown at 212, during one more additional cycles.

FIG. 8 shows exemplary data that may be obtained using method 200 of FIG. 7. Each of the four dNTPs (including polymerase) are dispensed stepwise, shown at 220, to a pair of nanowire assemblies 222. Graph 224 plots each nucleotide reagent dispensed, shown at 226, against the conductance measured after each addition, shown at 228. An increase in conductance during and after contacting with a particular nucleotide signifies a partner nucleotide, complementary to the particular nucleotide, at the corresponding position in the template strand. The size of the increase signifies how many nucleotide subunits were attached, with the increase being generally proportional to the number of nucleotide subunits attached to each primer molecule of a nanowire assembly. Accordingly, the upper plot, shown at 230, indicates covalent addition of AGGTTCAA, and the lower plot, shown at 232, indicates covalent addition of GAGTCCA (and thus the presence of complementary sequences at corresponding regions of the template).

Example 4. Nanowire-based Analysis Utilizing Ligation

Figure 9:
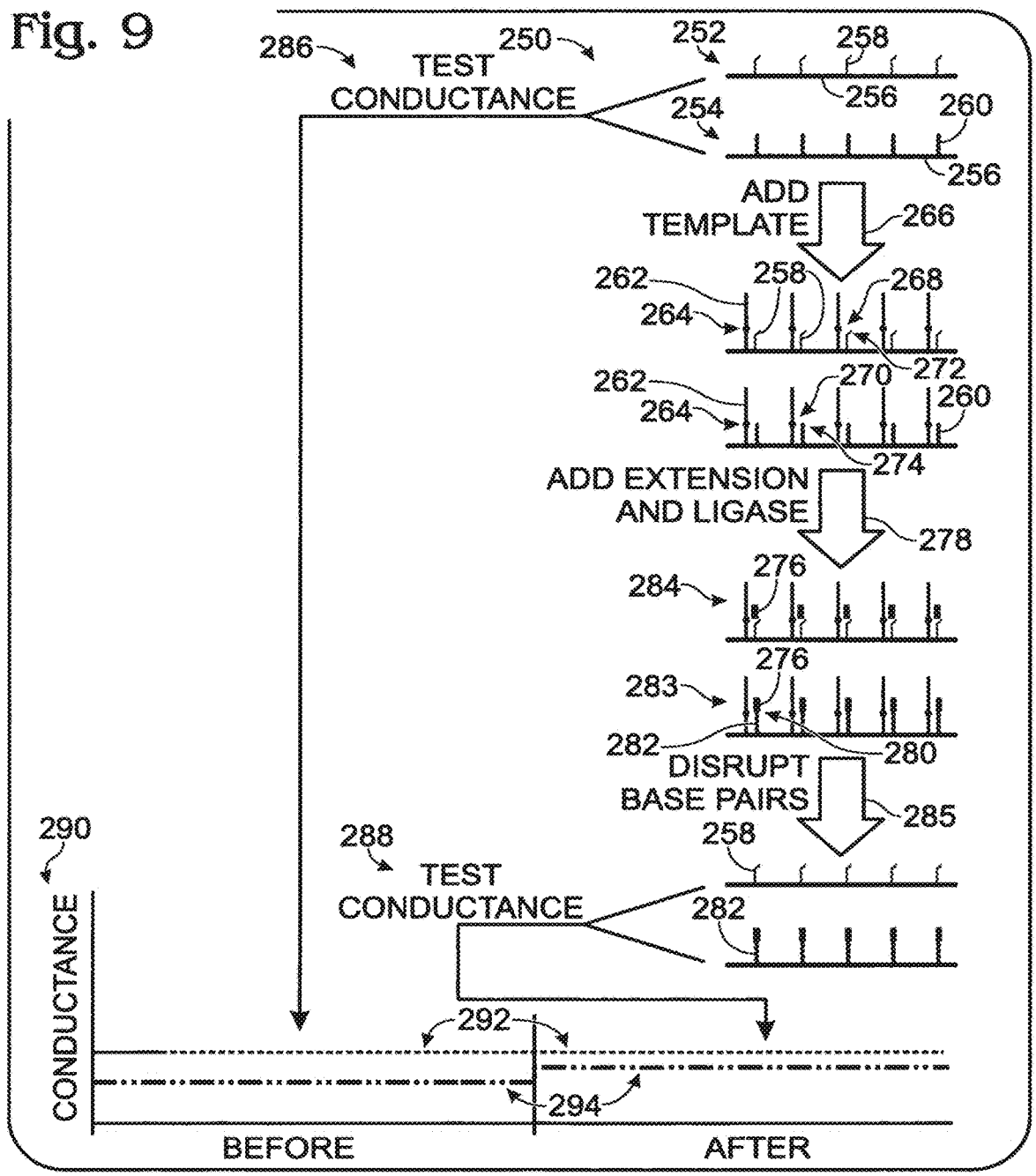
FIG. 9 is a somewhat schematic flowchart of an exemplary method of nanowire-based analysis of nucleic acids using ligation, in accordance with aspects of the present teachings.

This example describes nucleic acid analysis using ligation of nucleic acids associated with nanowires; see FIG. 9.

Humans have substantially identical genomes. Accordingly, positions of sequence variation within the population (e.g., single-nucleotide polymorphisms) can be utilized to identify individuals or lineages (e.g., for forensic purposes), to diagnose genetic diseases or conditions, and/or to predict responses to treatment regimens (e.g., to facilitate selection of drugs), among others. Ligation-based analysis can be suitable for sequencing individual positions of sequence variation in the population. In particular, ligation-based analysis can utilize the largely known sequence of a nucleic acid analyte to generate probes that allow sequencing of nucleotide positions of known variation among individuals of a population.

FIG. 9 shows a flowchart 250 for a method of nanowire-based sequencing using ligation, and exemplary data that may be obtained using the method.

Nanowire assemblies 252, 254 can be provided. The assemblies can include a nanowire 256 and a different probe 258, 260 coupled to each nanowire. The probes can include a region of nucleotide sequence variation in the human population. In particular, the probes (or a region thereof) can differ by only one (or a few) nucleotides, with each probe corresponding to a different sequence version of a polymorphism in the population. Furthermore, the sequence differences between the probes can be disposed at or near the end of the probes, so that any nonpairing of the probe with a template will be pronounced at the end of probe.

A template 262 having a polymorphic nucleotide 264 (in the population) can contact, shown at 266, the nanowire assemblies. The template can base pair with each of the probes to form nucleic acid duplexes 268, 270. However, probe 258 can be partially unpaired in duplex 268, shown at 272, because this probe does not form a base pair with the polymorphic nucleotide. Probe 260 is fully paired with the template in duplex 270, shown at 274, because this probe does form a base pair with the polymorphic nucleotide.

An extension nucleic acid 276 and a ligase enzyme can contact, shown at 278, the nanowire assemblies. The extension nucleic acid can be a (5'-phosphorylated) oligonucleotide configured to pair with the template in a position adjoining each probe. Accordingly, apposed ends of the extension nucleic acid and the probe can be joined by the ligase enzyme, shown at 280, to produce a ligation product 282 that is an extended version of probe 260 in assembly 283. However, ends of the extension nucleic acid and probe 258 are not substantially apposed for efficient ligation in assembly 284.

Nucleic acid duplexes can be disrupted, shown at 285. This disruption can leave original probe 258 and ligation product 282 coupled to their respective nanowires, while releasing the template from both nanowires, and the (unligated) extension nucleic acid from only the upper nanowire.

Conduction of the nanowires can be tested before and after the series of operations, shown at 286 and 288, respectively. Exemplary data that may be obtained is plotted in a graph 290. Probe 258 was not lengthened by ligation, so conductance of its associated nanowire is not changed, shown at 292. Probe 260 was extended by ligation, so conductance of its associated nanowire is increased, shown at 294.

The method presented above can be modified in various ways. For example, a single probe can be used sequentially with different extensions. In particular, the probe can hybridize with the template adjacent the polymorphic nucleotide, and then different potential extension substrates, which hybridize to different versions of the polymorphic nucleotide can be added separately, and tested for their ability to be ligated to the probe.

Figure 10:
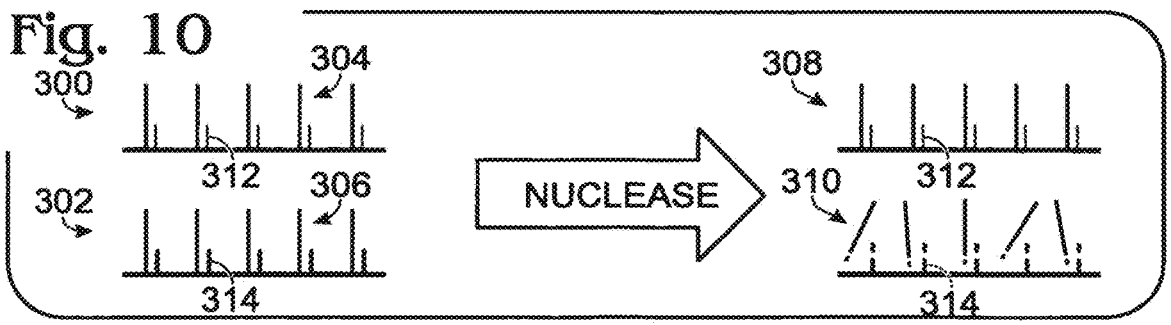
FIG. 10 is a somewhat schematic flowchart of an exemplary method of nanowire-based analysis of nucleic acids using cleavage, in accordance with aspects of the present teachings.

Further illustrative discussion of ligation conditions and other aspects of ligation are described, for example, in U.S. Pat. No. 6,511,810 (such as at column 17, line 58, to column 18, line 47), which is incorporated herein by reference Example 5. Nanowire-Based Analysis with Cleavage This example describes an exemplary nanowire-based system using selective cleavage of nucleic acids with a nuclease; see FIG. 10.

Nanowire assemblies 300, 302 including distinct nucleic acid duplexes 304, 306 can be distinguished by differential cleavage of the duplexes, shown at 308, 310, using a nuclease. The nuclease can selectively cut duplexes according to primary sequence, base-pair mismatches, unpaired ends, presence of a duplex, absence of a duplex, and/or the like. Differential cleavage of probes 312, 314 can be detected by measuring conductance of the nanowire assemblies with or without a separate duplex disruption step. In some examples, appropriate selection of probes can allow cleavage to be detected as a cleavage-induced destabilization of the duplex, as shown in the present illustration.

Example 6. Exemplary Coupling of Nucleic Acids to Nanowires

Figure 11:
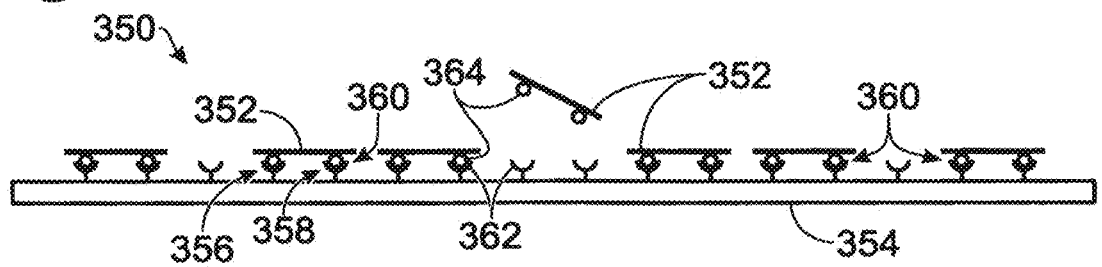
FIG. 11 is a somewhat schematic view of an exemplary nanowire assembly during coupling of a nucleic acid (an analyte and/or a probe) to a nanowire of the assembly at two or more spaced sites along the nucleic acid, in accordance with aspects of the present teachings.

This example describes an exemplary approach for coupling nucleic acids to nanowires at two or more sites along each nucleic acid; see FIG. 11.

Each nucleic acid (i.e., an analyte and/or a probe) can be coupled to a nanowire at one or more positions along the nucleic acid. In some examples, the nucleic acid can be coupled at two or more spaced sites (i.e., separated by one or more nucleotides of the nucleic acid). Coupling at multiple sites can constrain the nucleic acid to an orientation that is more parallel to the nanowire than coupling at a single site. Accordingly, the use of multiple coupling sites can position the nucleic acid closer to the nanowire, with less variation in spacing from the nanowire for different regions of the nucleic acid. Placing the nucleic acid closer to the nanowire, and in a more constrained configuration, can increase the sensitivity with which changes in an electrical characteristic can be measured, and also can reduce the variation in the changes measured with respect to different regions of the nucleic acid. As a result, the use of multiple coupling sites per nucleic acid molecule can allow a number of advantages over single-site coupling, such as (1) more sequence information (i.e., longer reads) for each analyte, (2) sequence analysis with fewer analyte molecules per nanowire, and/or (3) more consistent sequence analysis of analytes, among others.

FIG. 11 shows an exemplary nanowire assembly 350 during coupling of molecules of a nucleic acid 352 (an analyte and/or a probe) to a nanowire 354 of the assembly at two or more sites (e.g., sites 356, 358) along the nucleic acid. Each coupling site can be formed by a specific binding pair 360 (see Section III above). For example, nanowire 354 can be connected to a first binding member 362, and nucleic acid 352 can be connected to a second binding member 364 that binds specifically to the first binding member. Each molecule of the nucleic acid can be connected to (or integrally include) two or more moieties of the second binding member, to provide two or more binding sites along the nucleic acid. The moieties can be spaced from one another, for example, disposed generally toward opposing ends of the nucleic acid, to facilitate tethering two or more distinct regions of the nucleic acid to the nanowire. Exemplary first and second binding members can include, respectively, (1) streptavidin and biotin, (2) biotin and streptavidin, and/or (3) complementary nucleic acids, among others. If base-pairing is used to couple the nucleic acid to the nanowire at two or more spaced sites, spaced regions of the nucleic acid itself can be used for base-pairing interaction. A base-paired partner disposed at one or more of the spaced regions (and connected more directly to the nanowire) also can serve as a probe/primer, or a distinct probe/primer can be hybridized to the nucleic acid.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

We claim:

1. A method for sequencing a nucleic acid template, the method comprising:
   forming a set of nanowire assemblies each including a semiconductor nanowire and a first nucleic acid covalently bound to the semiconductor nanowire at two or more sites along the nucleic acid, the semiconductor nanowire connected at a first end to a first electrode and at a second end to a second electrode, a detector connected to the electrodes to detect an electrical characteristic of the semiconductor nanowire;
   contacting the set of nanowire assemblies with a second nucleic acid, the second nucleic acid forming a nucleic acid duplex with the first nucleic acid; and
   measuring an electrical characteristic of a nanowire assembly.

2. The method of claim 1, wherein the first nucleic acid is connected to a first binding member and the semiconductor nanowire is connected to a second binding member that specifically binds to the first binding member.

3. The method of claim 2, wherein the first binding member or the second binding member is streptavidin and the second binding member or the first binding member is biotin.

4. The method of claim 2, wherein the first nucleic acid is connected to two of the first binding members at sites spaced along the first nucleic acid.

5. The method of claim 4, wherein the first binding members are spaced at opposite ends of the first nucleic acid.

6. The method of claim 1, wherein the second nucleic acid is a primer, the method further comprising:
   contacting the nanowire assemblies with a polynucleotide; and
   contacting the nanowire assembly with a type of nucleotide for each of four different types of nucleotides corresponding to the nucleotides guanosine, adenosine, thymidine, and cytidine.

7. The method of claim 1, further comprising, prior to measuring an electrical characteristic, disrupting the nucleic acid duplexes to render less stable nucleic acid duplexes single stranded.

8. The method of claim 7, wherein disrupting includes changing a temperature of the set of nanowire assemblies.

9. The method of claim 7, wherein disrupting includes adjusting an ionic strength of a solution surrounding the set of nanowire assemblies.

10. The method of claim 7, wherein disrupting includes changing the concentration of an organic solvent.

11. The method of claim 7, wherein disrupting includes enzymatically disrupting.

12. The method of claim 7, wherein disrupting includes changing an electric field of a nucleic acid assembly.

13. The method of claim 1, further comprising contacting the nucleic acid duplexes with an extension nucleic acid, the extension nucleic acid joining to the first nucleic acid.

14. The method of claim 13, further comprising contacting the nanowire assembly with a ligase enzyme while contacting the extension nucleic acid.

15. The method of claim 13, wherein the step of measuring includes a step of measuring substantially no change in the electrical characteristic of a select nanowire assembly, thereby indicating that the extension nucleic acid is not added to an associated probe.

16. The method of claim 13, wherein the step of measuring determines a change in the electrical characteristic correlating the joining of the extension nucleic acid to the probe.

17. The method of claim 1, wherein the second nucleic acid is a probe of a set of different probes that include a regions of nucleotide sequence variation in a population.

18. The method of claim 17, wherein a variation in the region is disposed at or near an end of the probe.

19. The method of claim 17, wherein the nucleotide sequence variation corresponds to a polymorphism in a population.

20. The method of claim 1, further comprising forming a second nanowire assembly including a second semiconductor nanowire and a third nucleic acid covalently bound to the second semiconductor nanowire at two or more sites along the nucleic acid, wherein the nucleic acid assembly includes the first nucleic acid having a first region with a first nucleotide sequence variation and the second nucleic acid assembly includes the third nucleic acid having the region with a second nucleotide sequence variation.

* * * * *

UNITED STATES PATENT AND TRADEMARK OFFICE
CERTIFICATE OF CORRECTION

PATENT NO. : 10,961,575 B2  
APPLICATION NO. : 16/570093  
DATED : March 30, 2021  
INVENTOR(S) : Hongye Sun, Steven Fung and Sam Lee Woo Page 1 of 1

It is certified that error appears in the above-identified patent and that said Letters Patent is hereby corrected as shown below:

In the Claims

Column 18, Claim 17 Lines 40-41 the test "a regions" should read as --a region--

Signed and Sealed this  
Thirty-first Day of August, 2021

Drew Hirshfeld  
*Performing the Functions and Duties of the*  
*Under Secretary of Commerce for Intellectual Property and*  
*Director of the United States Patent and Trademark Office*